(12) United States Patent
Shifrin

(10) Patent No.: US 7,513,873 B2
(45) Date of Patent: Apr. 7, 2009

(54) LOW-NOISE ULTRASOUND METHOD AND BEAMFORMER SYSTEM FOR DOPPLER PROCESSING

(75) Inventor: Lazar A. Shifrin, San Jose, CA (US)

(73) Assignee: Supertex, Inc., Sunnyvale, CA (US)

( * ) Notice: Subject to any disclaimer, the term of this patent is extended or adjusted under 35 U.S.C. 154(b) by 612 days.

(21) Appl. No.: 11/243,775

(22) Filed: Oct. 4, 2005

(65) Prior Publication Data
US 2006/0079784 A1  Apr. 13, 2006

Related U.S. Application Data

(60) Provisional application No. 60/617,386, filed on Oct. 8, 2004.

(51) Int. Cl.
*A61B 8/14* (2006.01)
(52) U.S. Cl. ...................... 600/457; 600/437
(58) Field of Classification Search ............. 600/437, 600/457, 455
See application file for complete search history.

(56) References Cited

U.S. PATENT DOCUMENTS

| 4,866,613 | A | | 9/1989 | Amemiya et al. |
| 4,911,171 | A | | 3/1990 | Uchibori |
| 5,555,534 | A | * | 9/1996 | Maslak et al. ............... 367/135 |
| 5,562,097 | A | | 10/1996 | Yao |
| 5,664,575 | A | * | 9/1997 | Banjanin et al. ............ 600/455 |
| 5,964,708 | A | * | 10/1999 | Freeman et al. ............ 600/447 |
| 6,527,722 | B1 | | 3/2003 | Fazioli et al. |
| 6,544,180 | B1 | | 4/2003 | Doten et al. |
| 6,648,826 | B2 | | 11/2003 | Little et al. |

* cited by examiner

Primary Examiner—Eric F Winakur
Assistant Examiner—Katherine L Fernandez
(74) Attorney, Agent, or Firm—Jeffrey D. Moy; Weiss & Moy, P.C.

(57) ABSTRACT

An ultrasonic low-noise analog beamformer for Doppler acquisition achieves high sensitivity by translating the frequency of the ultrasound echoes to an intermediate frequency, which is well above of the 1/f corner. This is accomplished by beamforming the downconverted RF signals instead of using their baseband representation. The baseband conversion, succeeding the beamformation, also incorporates the steps of clutter filtering and anti-aliasing. The invention is particularly suitable for low-voltage process technologies that support broadband applications.

17 Claims, 5 Drawing Sheets

LOW-NOISE ULTRASOUND METHOD AND BEAMFORMER SYSTEM FOR DOPPLER PROCESSING

RELATED APPLICATION

This patent application is claiming the benefit of U.S. Provisional Patent Application having a Ser. No. 60/617,386, filed Oct. 8, 2004 in the name of Lazar A. Shifrin, and entitled "Low-Noise Ultrasound Method and Beamformer System for Doppler Processing".

BACKGROUND OF THE INVENTION

1. Field of the Invention

This invention relates to coherent ultrasound imaging systems and, more particularly, to phased array ultrasound imaging systems operating in different scan formats and imaging modes. Specifically, but not limited to, the invention relates to phased array beamformer system with low-noise Doppler data acquisition.

2. Description of the Related Art

Medical ultrasound imaging systems are capable of many different modes of operation. One of these is the Doppler mode dedicated to displaying the movement of blood within a vein or an artery.

Doppler imaging can be performed using either continuous wave (CW) or pulse wave (PW) techniques. In CW Doppler acquisition, the ultrasound transmitter continuously insonifies the body, while the receiver continuously receives echoes from all objects within the receiver's area of sensitivity. In this case, information received from any specific range interval cannot be isolated. Accordingly, the observation region is the overlap portion between the transmitting and receiving transducer beam profiles. To select the desired target, the instrument's area of sensitivity is adjusted, by either physical placement of the probe, by beamforming, or both.

As a single scatterer passes the observation region, the scatterer generates a burst of oscillations that contributes to the received radio frequency (RF) signal. The frequency of this oscillation is different from the transmit frequency because of the Doppler shift, which is proportional to the component of the blood velocity along the phase gradient of the combined transmitter and receiver beams. The "sign," or relative polarity, of the frequency difference between the transmitted and received signals determines the direction of the blood flow.

In PW mode, the scanner transmits a periodic pulse wave at a certain operating frequency $F_0$ that is directed to a particular location having blood flow. The signal reflecting from the moving blood is shifted in frequency by an amount proportional to the velocity of the blood flow. Thus, with the PW Doppler technique, the received signal has the same essential properties as for the CW. The difference is that the range gate limits the observation region along the beam to the range cell. This allows one to obtain only samples of the Doppler signal with the pulse repetition frequency, the PRF, which introduces the problem of frequency aliasing. Besides, due to limitations in the PRF rate, PW Doppler has limited ability to measure very high blood flow velocities. The rate limitations are fundamental because the transmitted pulse must reach the target and echoes are reflected back to the receiver before the next pulse can be sent.

CW Doppler, on the other hand, transmits a constant continuous wave signal toward the area to be imaged at a particular transducer operating frequency. The signal is continuously reflected by the blood flow and received by a receiver. The receiver distinguishes between the transmitted signal and the received signal by determining if there is a frequency shift between the transmitted and received signals. The movement of the blood causes this frequency shift, where its value is proportional to the velocity of the blood. The direction of the blood flow is dependent on whether the frequency of the received signal is greater or less than the frequency of the transmitted signal. Because the signal is transmitted continuously, CW Doppler can detect significantly higher frequency shifts than PW Doppler since there is no inherent sampling rate limitation.

There are two sources contributed to an RF signal received from an internal structure of human body containing a blood vessel. First, this is a strong signal from slowly moving tissue with low Doppler shifts (0 Hertz for stationary tissue). The Doppler signals from blood can be 60-100 dB weaker exhibiting larger shifts in frequency because the blood has higher velocities than the tissue. FIG. 2a illustrates these differences.

In comparison with PW Doppler, it is more difficult for CW techniques to distinguish between the transmitted signal and the reflected signal originated by moving blood. First, since the transmitted signal is continuous and relatively high in amplitude, it generates interference in the receiver. Second, the high-amplitude echoes reflected from stationary tissue, typically called "clutter," do not contain a frequency shift but occur simultaneously with the signals that represent blood flow. Further, conventional CW Doppler processors have a limited dynamic range due to the limited dynamic range of the analog-to-digital converters (ADCs). Thus, the clutter filtering that precedes the ADC must be much more complex, so that the signal that feeds the converter contains as little clutter content as possible.

There are numerous methods and techniques that have been developed to enhance quality of Doppler data acquisition. The following U.S. Patents represent typical examples of prior art, merely by way of example: U.S. Pat. Nos. 4,866,613, 4,911,171, 5,555,534, 5,562,097, 6,544,180, 6,527,722, and 6,648,826.

In general, the separate analog-processing path for a CW Doppler receiver consists of cascaded stages of mixers and filters. To support a variety of transducers, the hardware includes a number of programmable filters that are tuned to the operating frequencies of the available transducers. Such architecture requires using expensive switches and precision components. For the phased array, i.e., multi-channel ultrasound systems, it causes a substantial increase in the component count and cost that makes this approach impractical.

To address the complexity issue, Fazioly, et al., U.S. Pat. No. 6,527,722, describes a CW Doppler single channel receiver consisting of a mixer accompanied by a bandpass filter (BPF), which operates to translate the RF input signal to a constant intermediate frequency (IF) signal. Consequently, the cost of the CW Doppler processing circuitry will be reduced with respect to a conventional processing system. However, referring to a single-channel receiver, Fazioly does not disclose any aspect of CW Doppler data acquisition with a phased-array transducer.

Maslak, et al., U.S. Pat. No. 5,555,534, teaches a phased array receive beamformer that is dedicated to operate in both CW and PW Doppler modes. FIG. 1 depicts a block diagram of the beamformer comprising a plurality of receive channels 110. Each of the channels includes a low-noise amplifier (LNA), a gated quadrature mixer, and a complex rotator. In operation, the RF signal amplified by LNA 111 is mixed in a quadrature mixer with a pair of clocks being out of phase by 90° with respect to each other. The in-phase clock signal $LO_I$, which is supplied to mixer 102, is provided in common to the in-phase mixers of all of the analog receive channels 110, as is the quadrature clock signal $LO_Q$ received by mixer 104. The outputs of the mixers 102 and 104 are in-phase and quadrature-phase components of a complex baseband signal related to respective RF echo. These outputs are coupled to a complex rotator 106, which is a baseband signal processing block, that weights, selects, and sums the in-phase and quadrature-phase components. The I/Q outputs of the rotator are programmed to represent eight possible phases of the input complex signal. The rotator in each channel has its own set of three phase control input bits.

Referring to FIG. 1 again, the in-phase (I) signals 108 of all of the individual Doppler receive beamformer channels 110 are summed in four groups. At first, the per-group signals 108 are applied to respective summers 112 having a low-pass pole 114, which filters out the RF products of the mixing process without affecting the baseband component. Then, the partial sums 118 are combined by a summer 116 to generate a beamformed in-phase signal 120 from all channels. It will be understood that the quadrature signals are combined in the same manner.

The outputs of the I/Q summers are coupled to a downstream processor 140. The processor comprises in-phase and quadrature sections but since they are identical, only the in-phase section is shown. It includes an integrator 122 to integrate (PW) or to smooth (CW) the beamformed signals, a track-and-hold circuit 124, a high-pass filter 126 to remove clutter signals, an anti-aliasing filter 128, and an ADC 130 to convert the relatively clutter-free signals to digital format.

As known in the art, there are indisputable advantages of the baseband representation of composite RF signals similar to those shown in FIG. 2a. However, since blood flow originates a Doppler shift in the audible range, the spectrum of the baseband I/Q components occupies the same frequencies as flicker or 1/f noise. For reasons, which will become apparent, the overlapping of spectra as shown in FIG. 2b may substantially reduce the dynamic range of D-mode acquisition.

There are two main sources of the 1/f noise in the '534 beamformer:

First, the per-cannel quadrature mixers, 102 and 104, comprise two transistor pairs switching at the LO frequency. While switching, the gates (bases) of the pair exhibits charge fluctuations. Having a spectral density proportional to 1/f, these fluctuations are transferred to the output by multiplication with a time-varying transconductance of the switching pair. Since transconductance of the pair is varied at the 2×LO frequency, it contains only even-order harmonics of the LO. This means that flicker noise from the switching pair will directly appear at the output around DC, i.e., in baseband. (Sometimes this noise is referred as the phase noise.) For an N-channel beamformer, the resulting 1/f noise from switching is increased for a factor of $N^{1/2}$ as compared with a single channel. However, since the beamformer signal gain is equal to N, the signal-to-noise ratio (SNR) is improved by a factor of $N^{1/2}$.

Another source of flicker noise is subsequent summing inherently associated with the process of beamforming. Referring to '534 in particular, the complex rotator 106 sums the weighted baseband outputs of the mixers 102 and 104. It is followed by the combining of all of the per-channel I/Q output signals represented in the baseband. The noise-referred details of the summing operation are discussed below.

It will be evident to those skilled in the art that the LNA/mixer combination needs to provide a gain, which is sufficient to prevent substantial degradation of the SNR by the noise introduced by subsequent summing means. However, a weak signal representing blood flow is situated on a top of a high-amplitude clutter, which may be in the range of 500 millivolts peak-to-peak. Consequently, the entire signal-processing chain needs to be relatively high-voltage in order to avoid signal clipping.

By contrast, the latest integration technology is based on low-voltage MOS processes with signal swing of 1.8 Volts or less. Thus, developing an integrated MOS receiver for D-mode, the LNA/mixer gain may not exceed 12 dB. For a given gain G, the expected SNR degradation due to 1/f noise can be found as follows:

Let $f_C$ denote flicker noise corner frequency, i.e., the frequency at which 1/f noise exceeds thermal noise. Depending on the operating conditions of the fabrication process, MOS devices manifest a corner frequency, which varies as the reciprocal of the channel length. Typically, $f_C$ has a range of 100 kHz to 1 MHz.

If $S_F$ and $S_T$ are the power spectral densities of 1/f noise and thermal noise, respectively, their densities can be equated at a corner frequency of $f_C$, i.e., $S_F(f_C)=S_T$. By definition, the power spectral density of 1/f noise is $S_F=K/f$. Resolving this formula for $f=f_C$ yields $K=S_T \cdot f_C$. It allows to express flicker noise spectrum as $S_F=S_T \cdot f_C/f$.

In addition to the phase noise, noise contribution from the LNA/mixer section is primarily related to translating LNA noise from the RF range (2 to 8 MHz, typically) to the baseband. Since the above RF range is well above the 1/f noise corner, the corresponding noise is representative of thermal noise. This noise manifests a noise floor for a subsequent stage, i.e., the summer 112. The noise-floor spectrum introduces by the LNA/mixer section is relatively flat with power spectral density of $G^2 \cdot S_T$. Because noise contributions from the switching pair and said noise floor are mutually independent, their influence can be considered separately.

At the summing node of 112, the resulting noise exhibits a linear combination of the above-mentioned noise floor and the input referred noise produced by the summer itself. If we consider the input referred noise to be originated by thermal and flicker sources, the total noise power can be expressed as the sum of three definite integrals, each related to respective noise source. To determine the limits of integration, it can be taken into account that the clutter filter removes any Doppler along with noise components occurring at or near 0 Hertz. Let $f_{MIN}$ denote a minimal frequency of a signal passing the clutter filter. On the other end, the highest Doppler shift determines a cut-off frequency of the processing, $f_{MAX}$. Typically, $f_{MAX}=100$ kHz. Thus, the total noise power, $V_N^2$, yields:

$$V_N^2 = \int_{f_{MIN}}^{f_{MAX}} S_T \, df + G^2 \times \int_{f_{MIN}}^{f_{MAX}} S_T \, df + \int_{f_{MIN}}^{f_{MAX}} S_F \, df$$

Evaluating the integrals, $$V_N^2 = S_T \left[ (1+G^2) \cdot (f_{MAX} - f_{MIN}) + f_C \cdot \ln\frac{f_{MAX}}{f_{MIN}} \right]$$

In the absence of flicker noise, the total noise power would be $V_{NT}^2$, where:

$$V_{NT}^2 = S_T(1+G^2) \cdot (f_{MAX} - f_{MIN})$$

Taking the ratio of $V_N$ to $V_{NT}$, the SNR degradation due to 1/f noise of the summer can be expressed as:

$$\gamma = \frac{V_N^2}{V_{NT}^2} = 1 + \frac{f_C}{(f_{MAX} - f_{MIN})(1 + G^2)} \cdot \ln\frac{f_{MAX}}{f_{MIN}}$$

TABLE I sets forth the amount of SNR degradation, γ, for $f_{MIN}$=1, 10, 100, and 1000 Hz with G=4 and $f_C$=1 MHz.

TABLE I

| | $f_{min}$ (Hz) | | | |
|---|---|---|---|---|
| | 1 | 10 | 100 | 1000 |
| γ(dB) | 8.906 | 8.074 | 7.044 | 5.692 |

It can be seen that flicker noise associated with subsequent summing stages increases the system noise floor by a factor of 7-8 dB that substantially degrades the performance of beamforming provided in the baseband.

As mentioned, the influence of 1/f noise can be minimized by increasing the LNA/mixer gain. However, in a low-voltage system this approach is practically inapplicable since clutter would desensitize the beamformer before the signals from blood flow become sufficiently large. Therefore, there is a need for a wide-dynamic-range phased array Doppler beamformer adapted to operate using sub-micron technology.

SUMMARY OF THE INVENTION

By way of introduction, the present invention includes a Doppler beamformation method and a beamformer system. The Doppler beamforming method allows one to achieve a wide dynamic range while operating in a low-voltage environment. The new Doppler beamformer outperforms the prior art by simplicity, versatility, lower cost, and higher power efficiency, while maintaining programmability for phase rotating.

In a first aspect, each of a plurality of RF signals is translated to an intermediate frequency (IF) by a mixer that modulates the RF input by a local oscillator clock (LO), IF is higher than the corner frequency, $f_C$.

In the second aspect, the phases of the produced IF signals are aligned by applying the LO clocks having a selectable angle.

In the third aspect, the aligned IF signals are coherently summed.

In the fourth aspect, the summed IF output is downconverted to the baseband.

Further aspect and advantages of the invention are discussed below in conjunction with the preferred embodiments.

BRIEF DESCRIPTION OF THE DRAWINGS

The invention will be described with respect to particular embodiments therefrom referring to the following drawings.

DETAILED DESCRIPTION OF PREFERRED EMBODIMENTS

In operation, receive beamformers apply controllable delays to the transducer signals prior to summing to steer and focus the receive beam. Referring to Doppler imaging, CW mode has no resolution along the range direction. However, it allows one to select a target of interest in the azimuth direction. Fundamentally, the related information is contained in the relative phasing of the RF signal across the channels. Accordingly, beamforming can be achieved through phase shifting of the received signals in a circular range of 0° to 360°.

The invention is best understood by reference to the figures wherein alike parts are designated with like numerals throughout. A description of the present invention is given with reference to FIGS. 2-5.

Figure 1:
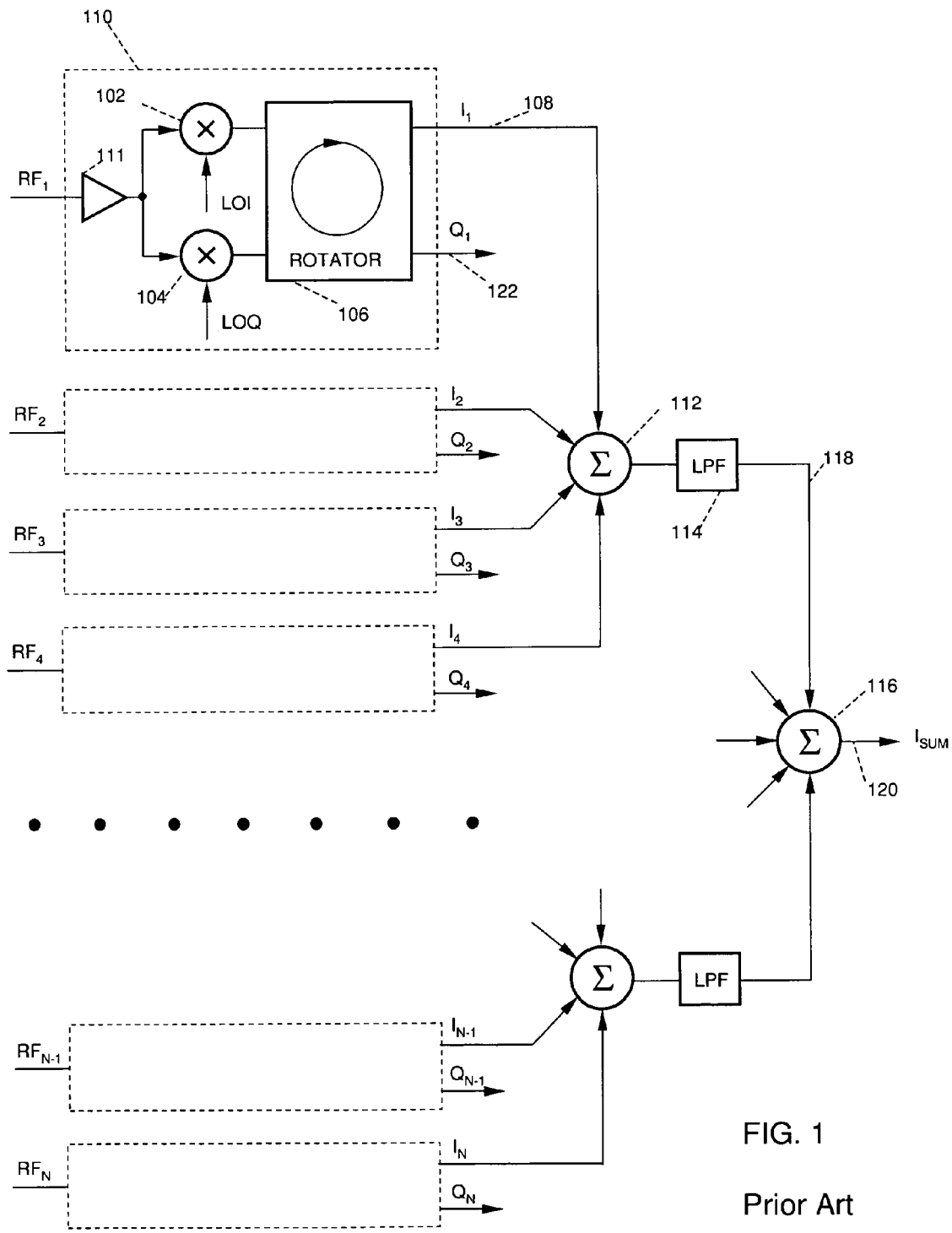
FIG. 1 is a block diagram of the ultrasound Doppler beamformer known in the art.
Figure 2:
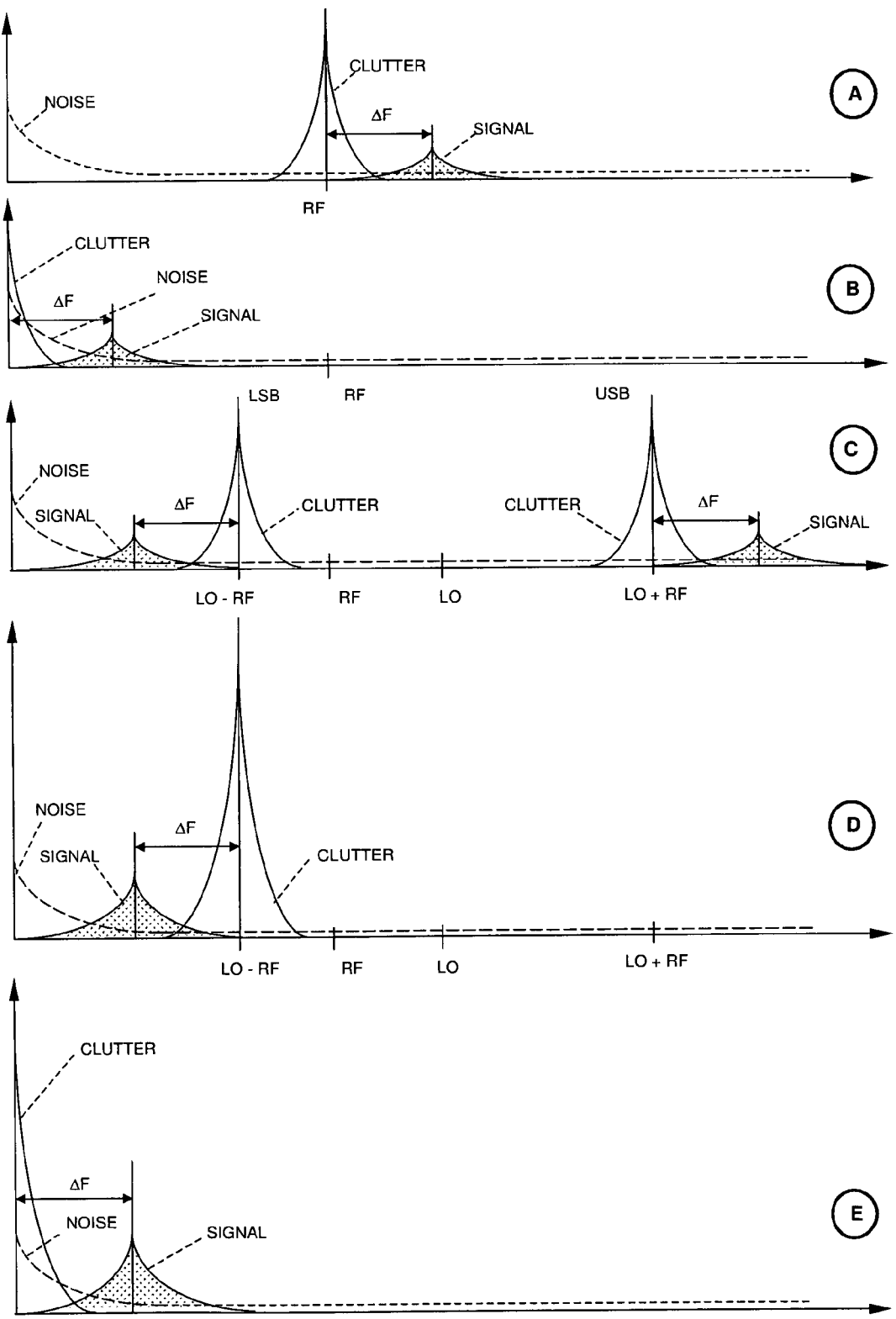
FIG. 2 illustrates arrangement of Doppler spectra and power spectrum of 1/f noise for a traditional baseband conversion and the proposed dual-conversion scheme.
Figure 3:
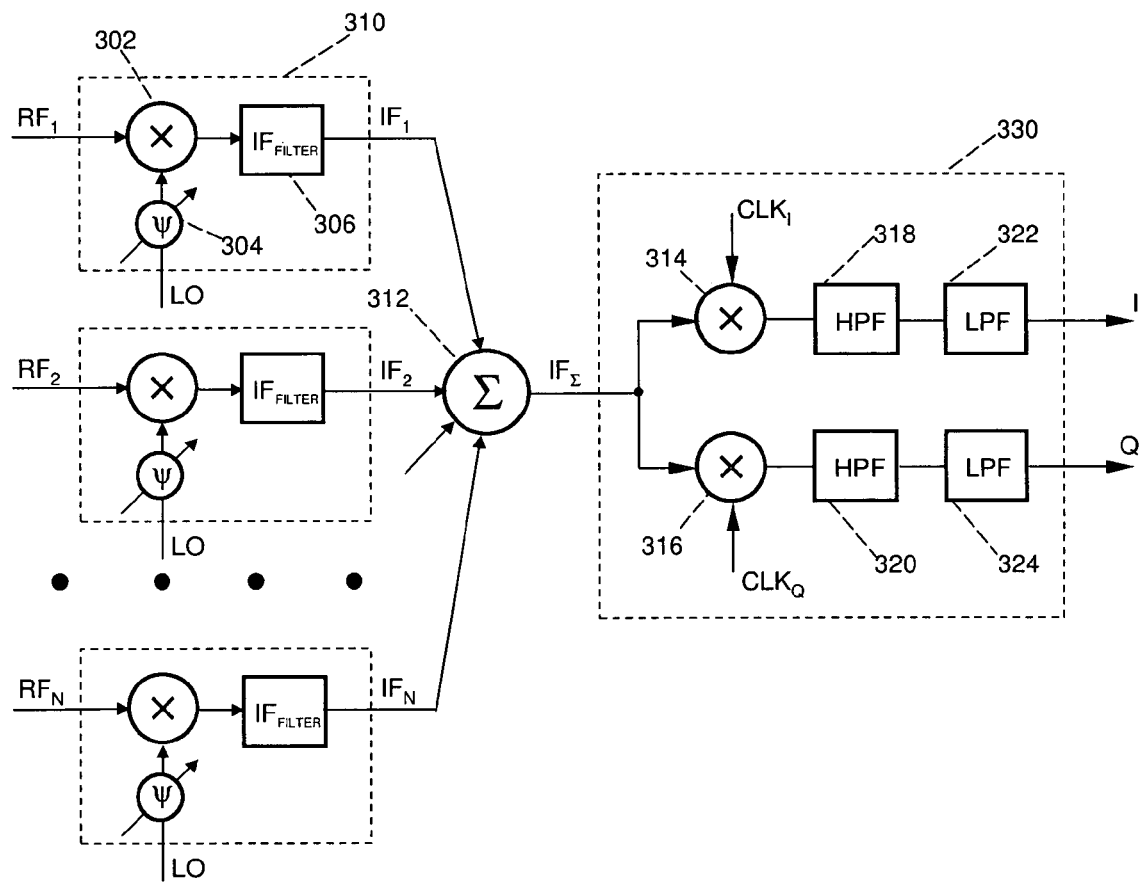
FIG. 3 is a functional diagram showing the relationship between the elements of a dual-conversion CW Doppler beamformer.

FIG. 3 is a functional diagram showing the relationship between the elements of a dual-conversion CW Doppler beamformer. Referring to the diagram, the proposed beamformer comprises a plurality of N identical Doppler channels 310, an N-input summer 312, and a downstream processor 330. Each of the channels 310 comprises a mixer 302, an IF filter 306, and a phase rotator 304.

Mixers 302 are operative to translate the frequency of the ultrasound echoes, $RF_1$-$RF_N$, to an IF. This is done by mixing input RF signal with a local oscillator (LO) clock. FIG. 2a illustrates the spectral contents of such a signal.

The ideal mixer is a device, which multiplies two input signals. If the inputs are sinusoids with frequencies denoted as $f_{RF}$ and $f_{LO}$, the ideal mixer outputs two spectrum lines at the intermediate frequencies $f_{RF}$+$f_{LO}$ and $f_{LO}$-$f_{RF}$. The sum and difference frequencies are usually associated with the upper (USB) and lower (LSB) sideband products of the mixing process, respectively. The upper and lower sidebands contain equivalent information as shown in FIG. 2c; thus, only one needs to be processed further. Correspondingly, either the USB, or the LSB products can be selected by filter 306 that produced a plurality of the IF signals, $IF_1$-$IF_N$.

Phase rotator 304 provides phasing of the LO clock on the per-channel basis. This allows to align the IF signals. Combining signals that have been aligned, summer 312 provides a beamformed output, $IF_\Sigma$, as shown in FIG. 2d. Since this combining occurs at an intermediate frequency, which is above the 1/f corner, flicker noise of the summer is virtually omitted.

The output of the summer 312 feeds the processor 330 operating in baseband. Processor 330 comprises two demodulators, 314 and 316, arranged for quadrature operation. To operate in quadrature, reference clocks of said demodulators, $CLK_I$ and $CLK_Q$, are out of phase by 90° with respect to each other. Both clocks are running at the IF rate. FIG. 2e depicts the baseband representation of the $IF_\Sigma$ signal when the outputs of both demodulators are summed geometrically.

Each of the demodulators is followed by two filters connected sequentially. There are a clutter (high-pass) filter 318 (320) and an anti-aliasing (low-pass) filter 322 (324). Removing strong clutter signals from surrounding slow-moving tissue, the high-pass filters reduce the dynamic range of the in-phase and quadrature components, thereby, better utilizing the dynamic range of two analog-to-digital converters (ADC) following the CW Doppler beamformer. The low-pass filters prevent aliasing of signals or noise, which frequencies exceed one-half of the converters' input sampling rates. Thus, the I/Q outputs of the downstream processor 330 primarily represent those echo signals that were originated by blood flow.

Figure 4:
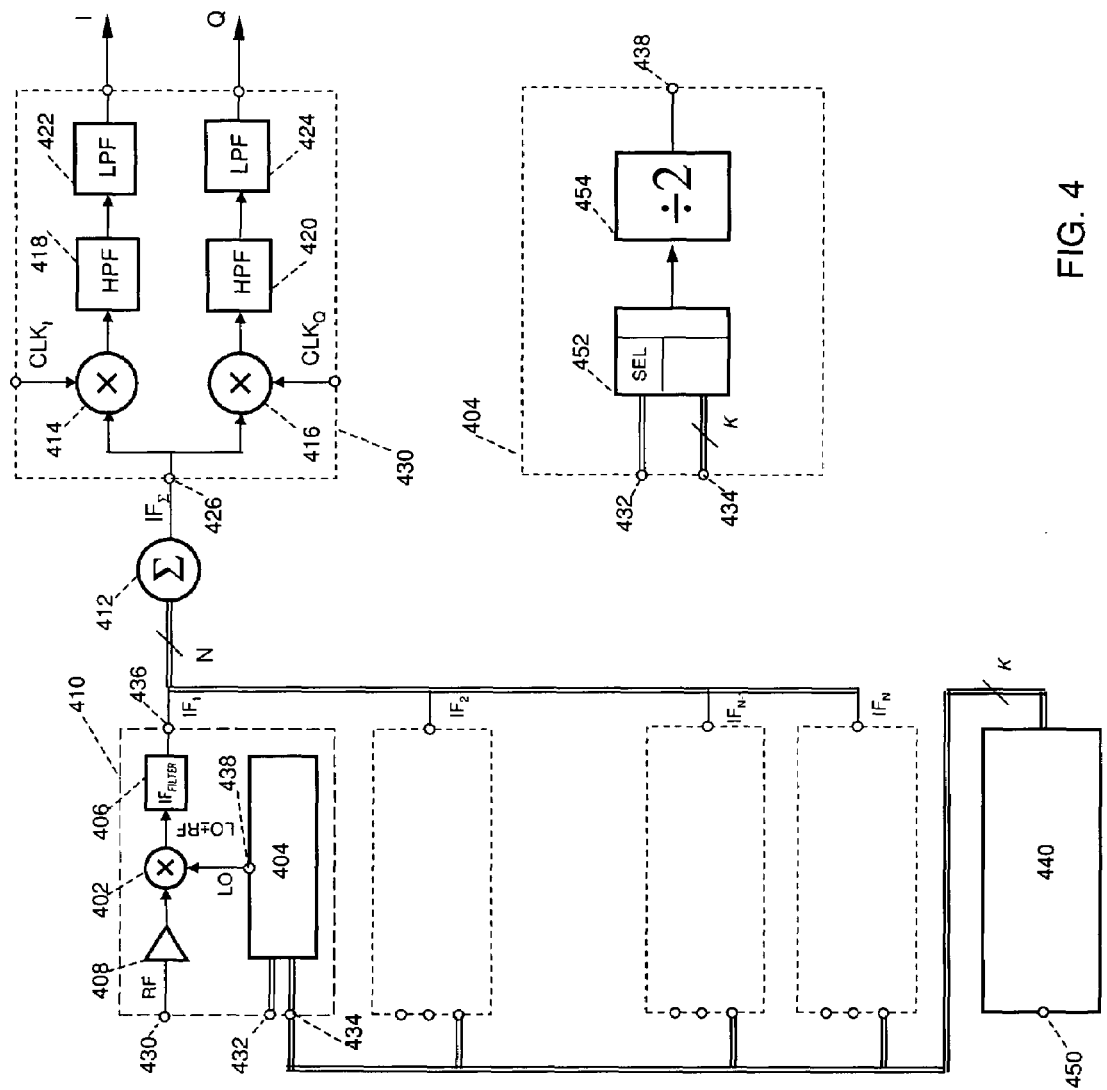
FIG. 4 is a block diagram of an embodiment of a low-noise beamformer system for CW Doppler imaging.

FIG. 4 depicts a detailed block diagram of an embodiment of a low-noise Doppler beamformer. Referring to the diagram, the beamformer comprises a plurality of N identical Doppler channels 410, an N-input summer 412, a downstream processor 430 having an input 426, and a multi-phase clock oscillator 440. The clock oscillator 440 provides a plurality of k phase-shifted LO clocks having their phases evenly spaced within a 360° range.

Each of the channels 410 comprises a buffer amplifier 408, a mixer 402, an IF filter 406, and a phase-selecting unit 404. As shown, amplifier 408, mixer 402, and filter 406 are connected sequentially. The LO clock applied to the mixer 402 is derived from the unit 404. Input 430 is operative to receive the RF signals. The IF outputs, $IF_1$-$IF_N$, are provided via nodes 436.

The phase-selecting unit 404 comprises a k-input multiplexer 452, a divide-by-2 counter 454, a clock terminal 434, a select port 432, and an output node 438.

In operation, terminal 434 receives the entire set of k phase-shifted LO clocks. Multiplexer 452 selects one of those in response to a predetermined binary value applied to the port 432. Then, the clocking frequency is divided by 2 in the counter 454 and outputted via the node 438.

Analytically, the process of frequency translation and phase alignment provided by a Doppler channel can be described as follows:

Let $RF_n = \cos(\omega_{RF} t + \Phi_n)$ denote an RF signal applied to the input 430 of n-th Doppler channel.

The LO clock appeared at the node 438 is:

$$LO_n = \cos(\omega_{LO} t - \theta_n)$$

where $\theta_n$ is the phase of the selected clock.

Multiplying the $RF_n$ signal with the $LO_n$ clock, the products are:

$$MIX_n = RF_n \cdot LO_n = \tfrac{1}{2} \cos[(\omega_{RF} + \omega_{LO})t + \Phi_n - \theta_n] + \tfrac{1}{2} \cos[(\omega_{RF} - \omega_{LO})t + \Phi_n + \theta_n]$$

To produce the $IF_n$ signal, either the upper or the lower sidebands of the $MIX_n$ signal will be filtered out. Thus, properly selecting $\theta_n$, the $IF_n$ signals can be aligned in phase.

Considering the clocking scheme, the multi-phase clock oscillator preferably comprises a k-phase (k/2-stage) twisted ring counter. The ring counter provides k clock lines from inverted and non-inverted outputs; these outputs are coupled to the inputs of the multiplexer 452 via the clock terminal 434.

The k-phase ring counter is fed via terminal 450 by an external clock at the rate of $2k \cdot f_{LO}$, where $f_{LO}$ is the LO frequency. For a given IF, $f_{LO} = f_{IF} + f_{RF}$.

Combining of the IF signals is provided by a summer 412 having a beamformed output, $IF_\Sigma$, connected to the input 426 of the downstream processor 430.

In brief, the downstream processor 430 replicates the arrangement of processor 330. There are two demodulators, 414 and 416. These demodulators provide baseband conversion of the beamformed IF signal, which is a single-channel RF signal translated in frequency and amplified by a factor of N/2 with virtually no extra noise.

As mentioned early, beamforming of the direct-converted ultrasound signals improves the SNR by a factor of $N^{1/2}$. Given the intensity of input-referred noise induced by the demodulator, the proposed dual-conversion Doppler beamformer would increase the SNR by a factor of N/2. To illustrate, for N=16, there is a 6 dB gain in SNR.

Continuing with the processor 430, the demodulators, 414 and 416, configured for quadrature operation. Accordingly, reference clocks of the demodulators, $CLK_I$ and $CLK_Q$, are out of phase by 90° with respect to each other. Both clocks are running at the IF.

Referring to FIG. 4 again, each of the demodulators is followed by a filter chain. This chain consists of a high-pass filter 418 (420) and a low-pass filter 422 (424). In essence, the purpose and operation of these filters are similar to those, i.e., 318, 320, 322, and 324, shown in FIG. 3.

Figure 5:
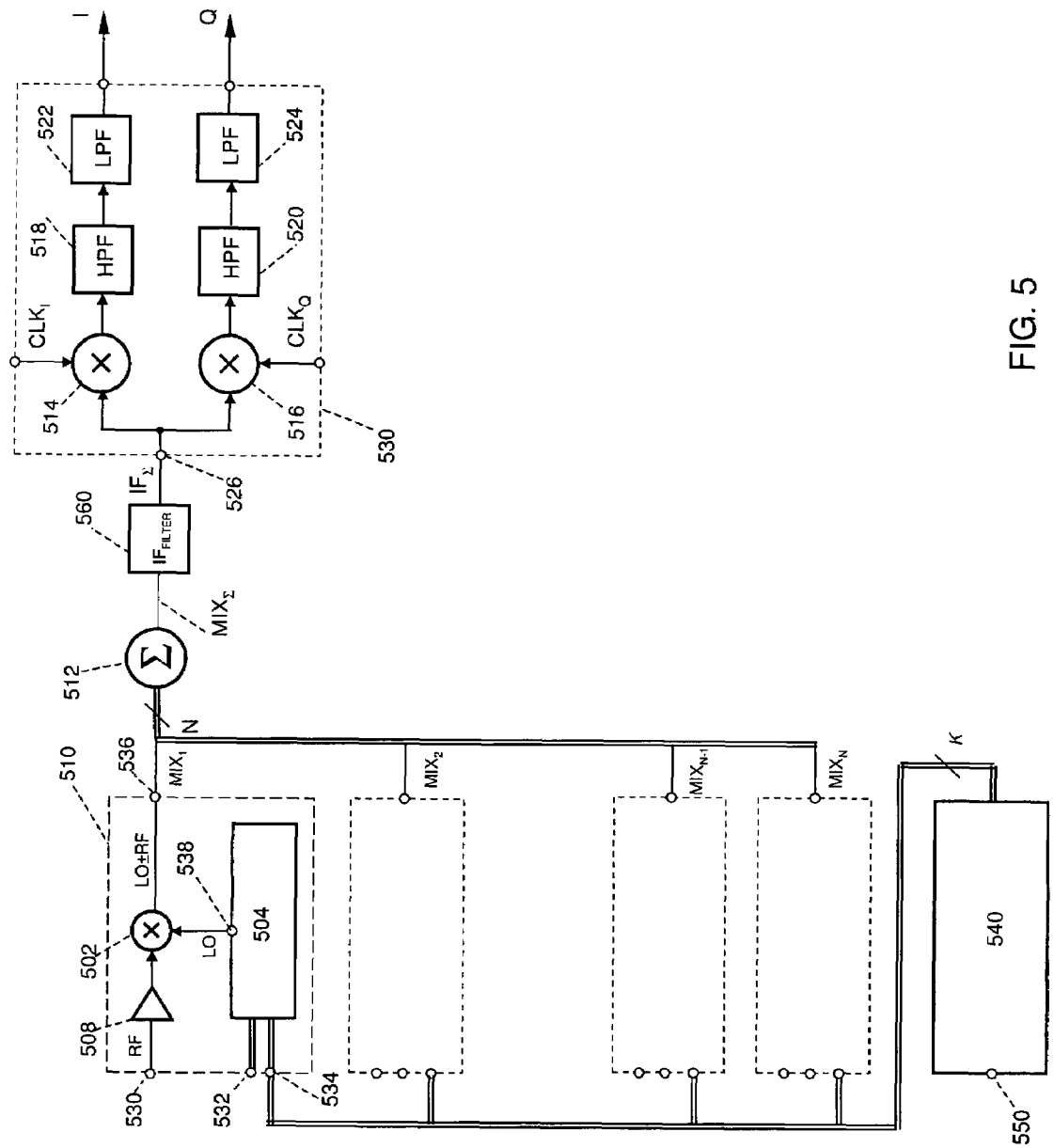
FIG. 5 is a block diagram of a second embodiment of CW Doppler beamformer.

The foregoing description of the beamforming process assumed identity of the Doppler channels. While this is essentially true for multi-channel ICs in terms of gain and delay matching, the deviation of the filter response because of component tolerances might be an important factor to consider. FIG. 5 depicts a second embodiment of CW Doppler beamformer allowing one to minimize the circuit sensitivity to variation in component values.

As illustrated, CW Doppler beamformer in FIG. 5 also comprises a plurality of N identical Doppler channels 510, an N-input summer 512, a downstream processor 530, and a multi-phase clock oscillator 540. Moreover, said summer, downstream processor, and clock oscillator are duplicates of respective units in FIG. 4.

Contradictory to the first embodiment, Doppler channel 510 has no IF filters but outputs both sidebands of the mixing process. Instead of per-channel filtering, there is a single IF filter 560 arranged to select either sideband of the beamformed signal $MIX_\Sigma$. This approach avoids the problem of channel identity at the expense of doubling the amplitude range of signals at the channel output.

Important advantages of the above embodiments of the present invention can be summarized as follows:

1. Implementing a direct-conversion CW Doppler beamformer, the spectrum of the per-channel quadrature components occupies the same frequencies as flicker noise. This overlapping substantially reduces the resulting SNR of D-mode acquisition.
2. Translating a received RF signal to an IF, beamforming may occur at the frequency range, which is above of the 1/f corner. Consequently, the proposed technique allows to improve the SNR as compared with prior art.
3. Summing multiple baseband signals, DC offsets, induced by mixers, could substantially reduce the range of beamforming linearity or, in the worst case, saturate the back-end stages. Representation of the per-cannel ultrasound echoes at the IF avoids this problem completely.
4. The proposed architecture is particularly suitable for low-voltage process technologies that support broadband applications.
5. The described embodiments employ phase-rotating at a fixed intermediate frequency, which makes it easier to predict and obtain repeatable performance of the entire system while implement a wide variety of transducers.

The foregoing description of the above embodiments of the present invention has been provided for the purposes of illustration and better understanding. It is not intended to be exhaustive or to limit the invention to the precise forms disclosed.

While the invention has been described above by reference to various embodiments, it would be understood that many changes and modifications could be made without departing from the scope of the invention. For example, different mixers, multi-phase clock generators, multiplexers, or buffer configurations may be used. It is therefore intended that the foregoing detailed description be understood as an illustration of the presently preferred embodiments of the invention, and not as a definition of the invention. It is only the following claims or added claims, including all equivalents, are intended to define the scope of this invention.

What is claimed is:

1. A method for receive beamforming in a CW Doppler ultrasound imaging system, comprising the steps of:
    generating a plurality of RF ultrasound signals from a respective plurality of N transducer elements incorporated in an array;
    receiving the plurality of RF ultrasound signals from the respective plurality of N transducer elements, said RF signals are characterized by a frequency, $f_{RF}$;
    translating the frequency of said RF signals to an intermediate frequency, $f_{IF}$, to produce a respective plurality of IF signals, said intermediate frequency is above the flicker noise corner frequency;
    aligning the plurality of IF signals by a predetermined phasing;
    summing said plurality of IF signals to produce a beamformed IF output; and
    downconverting the beamformed IF output to a complex Doppler signal, wherein each of the above steps is performed by said CW Doppler ultrasound imaging system.

2. A method according to claim 1, wherein said step of translating the frequency comprises the step of mixing the RF signals with a local oscillator (LO) clock signal ($f_{LO}$) and IF filtering.

3. A method according to claim 2, wherein the step of IF filtering is performed after the step of mixing, and wherein the step of downconverting is performed after the step of summing.

4. A method according to claim 2, wherein the step of IF filtering is performed after the step of summing, and wherein the step of downconverting is performed after the step of IF filtering.

5. A method according to claim 1, wherein said step of aligning comprises the steps of:
    calculating a desired delay profile across said plurality of transducer elements;
    computing the per-element IF phase shift in conformity with said delay profile;
    providing a predetermined set of LO clocks having their phases equally spaced in a range of 0° to 360°; and
    selecting an adequate LO clock signal, $f_{LO}$, for the IF phase shift using the best-fit criteria.

6. A method according to claim 5, wherein all LO clocks are displaced up in frequency by $f_{IF}$ with respect to a nominal transmit/receive frequency $f_{RF}$ so that $f_{LO}=f_{IF}+f_{RF}$.

7. A low-noise ultrasonic CW Doppler beamformer for processing a plurality of RF signals produced by a transducer array, comprising:
    a plurality of Doppler channels, each Doppler channel configured to receive an RF signal from a respective transducer element and to produce a phase-rotated signal at an intermediate frequency IF responsive to said RF signal and to a local oscillator clock;
    an N-input summer coupled to said plurality of Doppler channels for summing all of said phase-rotated signals and to produce a beamformed IF signal;
    a downstream processor coupled to said N-input summer configured to downconvert said beamformed IF signal and to provide an approximately clutter-free complex signal, said processor having an input signal terminal;
    a multi-phase clock oscillator coupled to said plurality of Doppler channels for providing a plurality of k phase-shifted LO clocks having their phases evenly spaced within a 360° range.

8. A low-noise ultrasonic CW Doppler beamformer according to claim 7, wherein said multi-phase clock oscillator is a k-phase (k/2-stage) twisted ring counter supplied by an external clock at the rate of $2k \cdot f_{LO}$.

9. A low-noise ultrasonic CW Doppler beamformer according to claim 7, further comprising at least one low-pass filter (LPF) having an input port and an output port, said LPF is operative to filter the IF signals and to cancel the high-frequency products above a cut-off frequency.

10. A low-noise ultrasonic CW Doppler beamformer according to claim 7, wherein each of said plurality of Doppler channels comprises:
    a buffer amplifier;
    a mixer coupled to said buffer amplifier configured to mix a buffered RF signal with a LO clock, said mixer having a signal port, a local oscillator (LO) port, and an output; and
    a phase-selecting means operative to select a LO clock from said plurality of k phase-shifted clocks.

11. A low-noise ultrasonic CW Doppler beamformer according to claim 10, wherein said phase-selecting means comprises:
    a divide-by-2 counter connected to the LO port of the mixer; and
    a multiplexer coupled to said divide-by-2 counter, said multiplexer comprising an output terminal providing a selected clock to said counter, a control port responsive for the clock selection, and k inputs.

12. A low-noise ultrasonic CW Doppler beamformer according to claim 10, wherein each of said plurality of Doppler channels further comprises an LPF, and wherein:
    the input port of said per-channel LPF connected to the mixer output;
    the output port of said per-channel LPF connected to a respective input of the summer; and
    the output IF node connected to the input terminal of said downstream processor.

13. A CW Doppler beamformer according to claim 9, wherein each of the Doppler channels arranged to apply the mixer output to a respective input of the summer directly, and wherein:
    the output IF node connected to the input port of a LPF; and
    the output port of said LPF connected to the input terminal of said downstream processor.

14. A CW Doppler beamformer according to claim 7, wherein said downstream processor further comprises:
    a first and a second clock terminals operative to provide a first and a second reference clocks, a first and a second demodulators, each having a signal port, a reference port, and an output, and wherein:
    the first and second demodulators operative to convert the beamformed IF signal to in-phase and quadrature-phase components, respectively;
    the signal ports of the first and second demodulators are coupled to said input signal terminal; and
    the reference ports of the first and second demodulators are coupled to the first and second clock terminals, respectively.

15. A CW Doppler beamformer according to claim 14, wherein said downstream processor further comprises:
    a first and a second filtering means connected to the outputs of the first and second demodulators, respectively, wherein each of said filtering means comprises a high-pass filter (HPF) and an anti-aliasing filter connected sequentially.

16. Downstream processor of claim 14, wherein said first and second reference clocks are in quadrature and running at the $f_{IF}$ rate.

17. A method for receive beamforming in a CW Doppler ultrasound imaging system, comprising the steps of:
   generating a plurality of RF ultrasound signals from a respective plurality of N transducer elements incorporated in an array;
   receiving the plurality of RF ultrasound signals from the respective plurality of N transducer elements;
   translating the plurality of RF ultrasound signals to a plurality of intermediate frequency (IF) signals, each of said plurality of IF signals being above the flicker noise corner frequency;
   aligning the plurality of IF signals by a predetermined phasing;
   summing said plurality of IF signals to produce a beamformed IF output; and
   downconverting the beamformed IF output to a complex Doppler signal, wherein each of the above steps is performed by said CW Doppler ultrasound imaging system.

* * * * *